United States Patent

Wong

[11] 4,096,388
[45] Jun. 20, 1978

[54] MEASURING GASEOUS OXYGEN WITH U.V. ABSORPTION

[75] Inventor: Jacob Y. Wong, Framingham, Mass.

[73] Assignee: Hewlett-Packard Company, Palo Alto, Calif.

[21] Appl. No.: 805,551

[22] Filed: Jun. 10, 1977

[51] Int. Cl.² .............................................. G01J 1/42
[52] U.S. Cl. ................................................ 250/373
[58] Field of Search .............. 250/372, 373, 343, 339; 356/51

[56] References Cited

U.S. PATENT DOCUMENTS

| 3,612,866 | 10/1971 | Stevens | 250/373 X |
| 3,976,883 | 8/1976 | Krakow | 250/373 X |
| 3,982,130 | 9/1976 | Trumble | 250/373 |

*Primary Examiner*—Davis L. Willis
*Attorney, Agent, or Firm*—Donald N. Timbie

[57] ABSTRACT

The concentration of oxygen in the presence of water vapor and other gases is measured without production of harmful levels of ozone by alternately passing ultraviolet light of two wavelengths through a sample, one of the wavelengths being strongly absorbed by oxygen and the other being weakly absorbed, and excluding light outside of these wavelengths.

11 Claims, 6 Drawing Figures

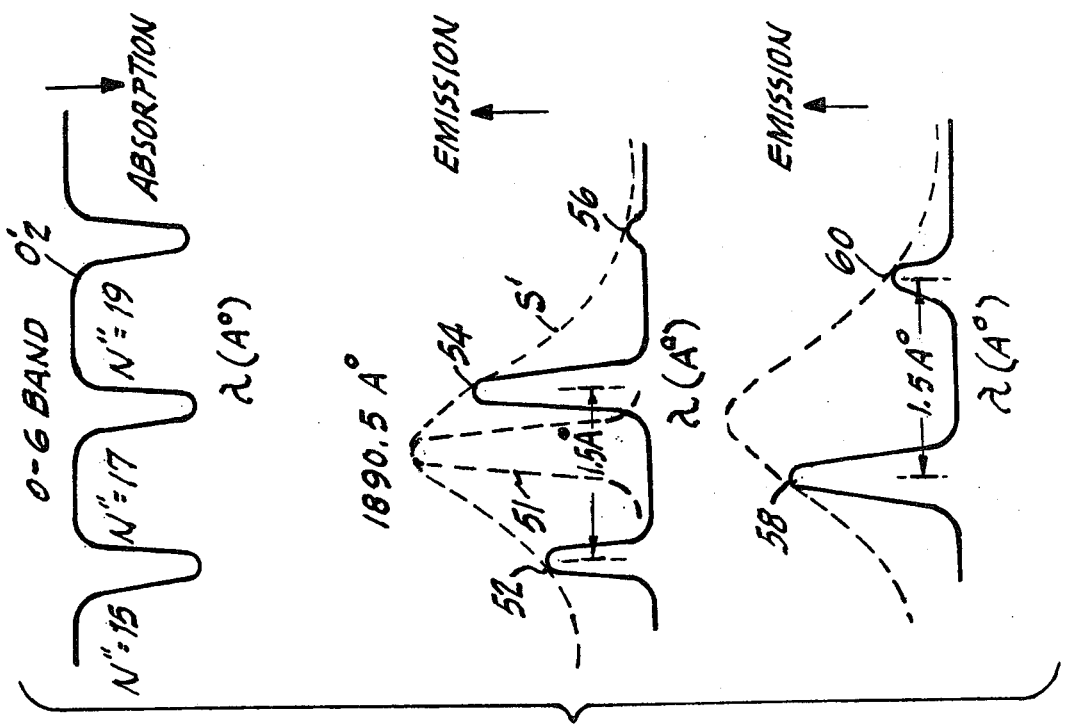
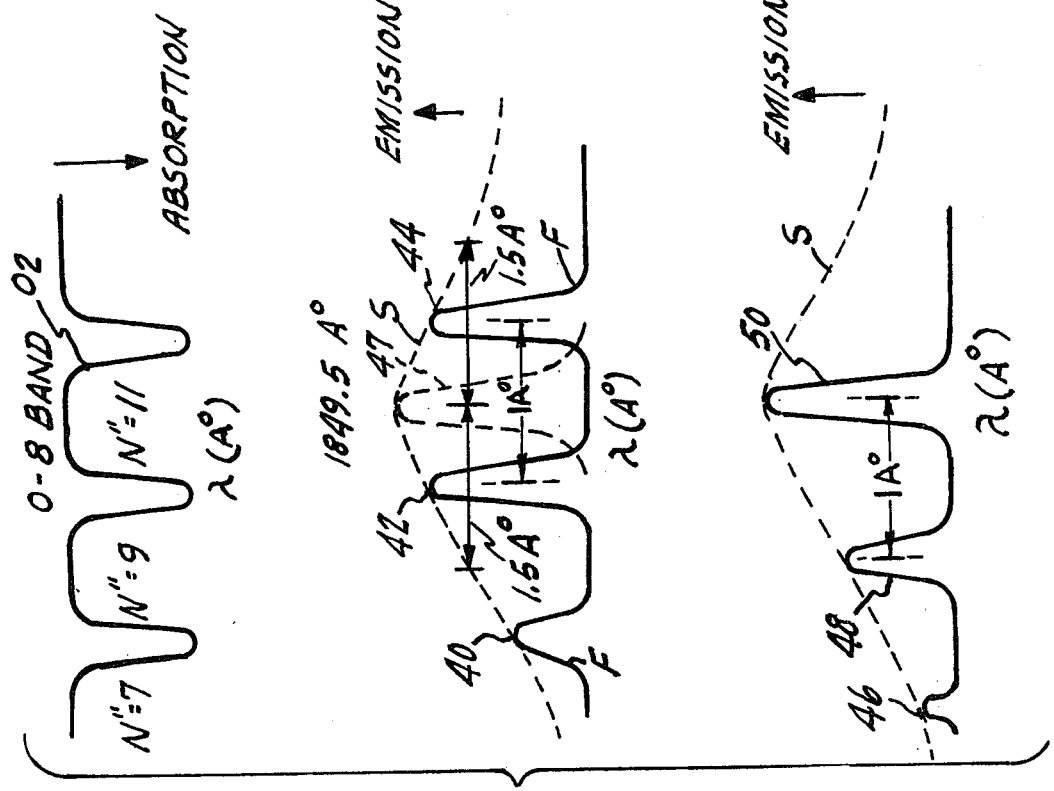
Fig.3.
Fig.2.

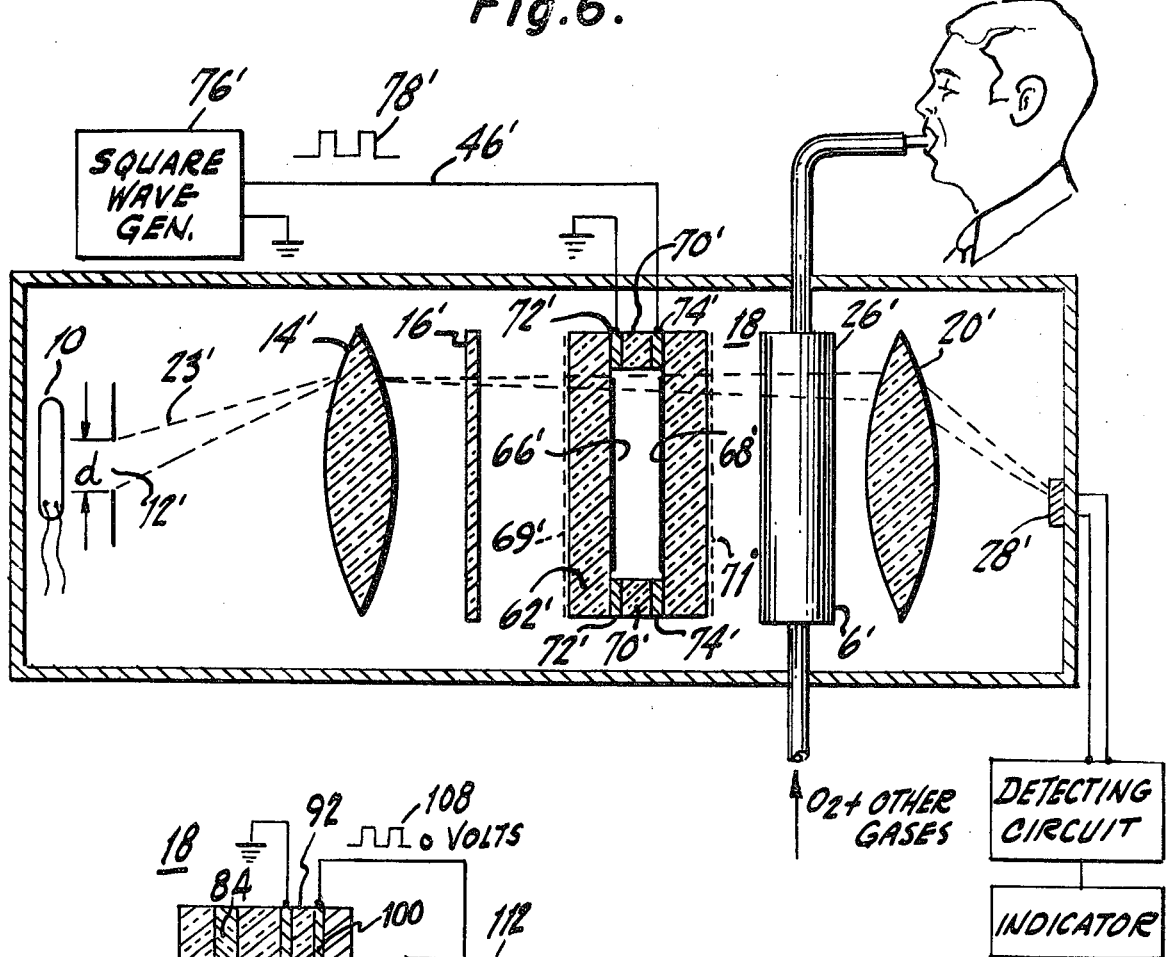

MEASURING GASEOUS OXYGEN WITH U.V. ABSORPTION

BACKGROUND OF THE INVENTION

The ability to monitor the concentration of oxygen in gases flowing in and out of the patient's lungs would be of invaluable assistance to the medical profession. Instruments for measuring the concentration of oxygen are available, but none has all the characteristics required, namely, a fast speed of response, sufficient accuracy and stability, freedom from malfunction in the presence of water vapor and other extraneous matter and the ability to operate in a stream of gas.

It has been suggested that concentration of oxygen can be determined by measuring the absorption of U.V. light, but this can result in the production of ozone in harmful quantities unless, as suggested by myself and Robert Chaney, all but one narrow emission band of U.V. light is filtered out. Unfortunately, the water vapor and other gases such as $CO_2$ usually present in the patient's breath also absorb the U.V. light of the selected narrow emission band so that their concentration must be determined by other instruments before the absorption due to the oxygen alone can be identified.

BRIEF DISCUSSION OF THE INVENTION

One way of carrying out the invention so as to accurately and safely measure the concentration of oxygen in the presence of water vapor and other gases is as follows. By known means the usual narrow spectral emission bands of a U.V. source are broadened so as to include light within each broadened band having a continuum of wavelengths including some that are strongly absorbed by oxygen as well as some for which the absorption is weak. One broadened emission band is selected by an optical bandpass filter and directed to an etalon filter that is controlled so as to pass U.V. light having wavelengths that are stongly absorbed by oxygen while in a first condition and to pass U.V. light of wavelengths that are weakly absorbed by oxygen while in a second condition. Both wavelengths are nearly equally absorbed by water vapor and other gases so that their effect can be eliminated by comparing the absorption measurements taken under the first and second conditions. The elimination of the other emission bands by the optical bandpass filter, prevents the production of ozone in harmful quantities.

BRIEF DESCRIPTION OF THE DRAWINGS

FIG. 2 shows the pertinent absorption peaks of $O_2$ and emission bands of U.V. light when an HgI lamp is used.

FIG. 3 shows the pertinent absorption peaks of $O_2$ and emission bands of U.V. light when an AsI lamp is used.

FIG. 4 shows a means of varying the angle between the normal of the etalon filter and the axis of the optical system in order to select the bands of wavelengths passed by the etalon filter.

FIG. 5 shows another means of varying the angle between the normal of the etalon filter and the axis of the optical system for achieving the selection of bands of wavelengths passed by the etalon filter, and FIG. 6 shows an alternate form of an instrument for measuring the concentration of oxygen in accordance with this invention.

DESCRIPTION OF A PREFERRED EMBODIMENT

Figure 1:
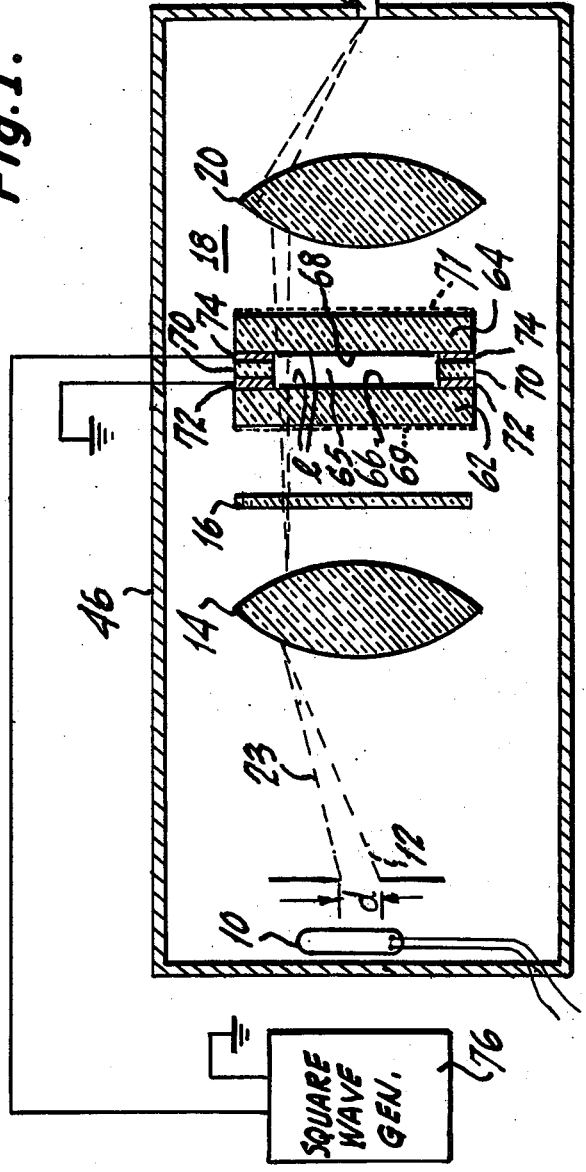
FIG. 1 shows a preferred form of an instrument for measuring the concentration of oxygen in accordance with this invention.
Figure 1:
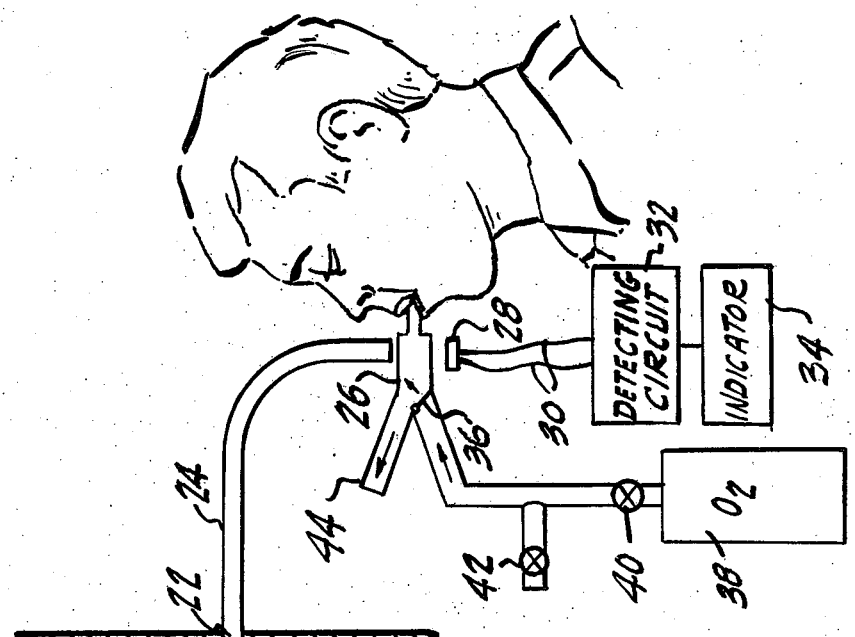

The preferred arrangement of a system for measuring the concentration of oxygen is illustrated in FIG. 1. U.V. light from a discharge lamp 10 passes through an input aperture 12 having a diameter d and is collimated by a lens 14 so as to pass through an optical band pass filter 16 and an etalon filter 18. It is then focussed by a lense 20 at an output aperture 22. One ray of U.V. light is indicated by the dotted line 23. A light pipe 24 is used to conduct the light from the output aperture 22 to one side of a transparent hollow tube or sample chamber 26 through which the patient breathes. A photodiode 28, used as a detector, is mounted to receive the light that passes through the tube 26 and produces a proportional electrical signal on its output leads 30. The leads 30 are connected to a means 32 for detecting the amplitude of an alternating current or voltage, and for processing it before applying it to an indicator 34. When the patient inhales, a hinged valve 36 opens to permit a mixture of oxygen from a tank 38 and air from the atmosphere, as determined by the setting of valves 40 and 42, to enter the sample chamber 26. When the patient exhales, the valve 36 moves to the position shown so that the exhaled air passes to the atmosphere through the tube 26 and a tube 44. Oxygen is kept out of the optical path between the lamp 10 and the output aperture 22 by enclosing the optical components in a case 46 that is either evacuated or filled with a gas, such as nitrogen, that does not absorb U.V. light of the wavelengths under consideration.

If the discharge lamp 10 is an HgI source, the situation is as shown in FIG. 2. Narrow spectral emission lines from such a source normally occur at 1849.57 A, 1930 A, 2537 A, 3125 A, etc. The emission at 1849.57 A is illustrated by the dotted curve 47. By controlling the pressure through Lorentz or collision broadening the emission lines can be broadened so that the emission at 1849.57 A appears as indicated by the dotted curve S of FIG. 2. It has a half width at half the maximum of $\sim 1.5$ A. U.V. light at the other emission lines is filtered out by the filter 16.

Some of the vibration-rotational absorption peaks $N'' = 7$, $N'' = 9$, and $N'' = 11$ of oxygen in the 0–8 band of the Schumann-Runge system are shown by the graph $O_2$ of FIG. 2. It will be noted that the natural emission line at the apex (1849.57 A) of the curve S is not aligned with any of the absorption peaks of the curve $O_2$ so that the portion of the incident light absorbed by oxygen flowing in and out of the tube 26 would be rather small. Furthermore, it will be found that other gases, and water vapor in particular, absorb enough light of this wvelength as to make gross error in the signal supplied by the diode detector 28. Therefore, in order to avoid the necessity of utilizing different apparatus for measuring the amount of water vapor and other gases so that their effect can be taken into account, the following procedure is followed in accordance with the invention.

In ways to be described, the etalon filter 18 can be made to have a first transmission characteristic wherein it selectively passes wavelengths of light within bands 40, 42, and 44 that are separated by $\sim 1$ A. Because the band 42 is precisely aligned with the absorption peak $N'' = 9$, and the other bands 40 and 44 are nearly in alignment with the absorption peaks $N'' = 7$ and $N'' = 11$, respectively, oxygen in the tube or sample chamber 26 absorbs a large portion of the incident light. Still, however, because it absorbs light at all the wavelengths involved, the ubiquitous water vapor and other gases interfere with the proper measurement of the concentration of the oxygen. Therefore, the filter 18 is abruptly changed so as to have a second transmission characteristic wherein it passes light in bands 46, 48 and 50 that are shown at the bottom of FIG. 2. As can be seen, these bands lie in the troughs between the peaks $N'' = 7$, $N'' = 9$ and $N'' = 11$ of the top curve $O_2$ where the absorption by oxygen is lowest. But the absorption by water vapor and other gases is still very nearly the same. Therefore, by comparing the signals generated by the diode detector 28 under this condition with the signals generated when the etalon filter 18 passes light within the bands 40, 42 and 44, the effect of water vapor and other gases can be eliminated, and a signal indicative of the concentration of oxygen can be provided. If the etalon filter 18 is made to alternate between its first and second transmission characteristics at a sufficiently high frequency, the diode detector 28 will produce an A.C. signal that can be detected so as to give an accurate instantaneous measurement of the concentration of oxygen flowing back and forth through the sample chamber 26. The comparison can be done in a number of ways but it is simple and effective to provide means for measuring the amplitude of the alternating current signals on the leads 30 and apply them to the amplifier and signal processor 32. The result of this comparison can be displayed by the indicator 34 which could be an ammeter, a digital panel meter or a cathode ray tube.

Should it be desired to use AsI in the lamp 10, the situation will be as depicted in FIG. 3. One of the sharp emission lines of AsI occurs at 1890.5 A, as shown by the dotted curve 51. By use of pressure in the lamp 10, the light emitted can be broadened about 1890.5 A as indicated by the dotted curve S'. The other emission lines are eliminated by the filter 16. The vibration-rotational absorption of oxygen in this range of U.V. light is greatest at peaks $N'' = 15$, $N'' = 17$, and $N'' = 19$ of the waveform $O_2'$ that are in the 0-6 band of the Schumann-Runge system. The peak of the light from the lamp 10 at 1890.5 A, is not precisely aligned with any of the absorption peaks, but the etalon filter 18 can be made to have a first transmission characteristic so as to pass light in bands 52, 54 and 56 that are very nearly aligned with the absorption peaks $N'' = 15$, $N'' = 17$, and $N'' = 19$ respectively. Under this condition the oxygen in the tube 26 absorbs a large portion of the light. The etalon filter 18 is then made to have a second transmission characteristic so as to pass light in the bands 58 and 60, shown at the bottom of FIG. 3. They fall in the troughs between the peaks $N'' = 15$, $N'' = 17$, and $N'' = 19$ of the curve $O_2'$ where the absorption by oxygen is lowest. In both cases, however, the amount of light absorbed by the water vapor and other gases is very nearly the same so that a comparison of the signal produced by the diode 28 under the two conditions yields the portion of the signal due to the presence of oxygen alone.

THE ETALON FILTER

Whereas the filter 16 need only have a pass band that is sufficiently narrow to exclude emissions of the lamp 10 at all but the emission line being used for measurement the filter 18 has to exhibit the much narrower pass bands shown in FIGS. 2 and 3. Such results might be attained with other optical filter means, but an etalon filter such as shown in FIG. 1 is preferred. It is comprised of a pair of circular transparent plates 62 and 64 having parallel opposed interior surfaces 66 and 68 that are mirrored so as to have a reflectivity R. Anti reflection coatings 69 and 71 can be deposited on the remote surfaces of the plates 62 and 64 in order to improve light transmission efficiency. The spacing L between these surfaces is determined by the thickness of an annulus 70 of piezoelectric material that has conductive material 72 and 74 deposited on opposite sides. One side is connected to ground and the other to a square wave generator 76 that provides square waves 78 that may have a typical frequency of 10 KHz.

The filter 18 is a Fabry-Perot type in which the transmission characteristics are determined by the refractive index of the gas or material in the gap between the mirrored surfaces 66 and 68, the separation L between them and their reflectivity R. If the gap is filled with air, the refractive index is 1.0002926. When the lamp 10 contains HgI, the operation illustrated in FIG. 2 is attained by making L equal to 0.0171 cm. The resulting transmission characteristics of the filter 18 is as indicated by the bands 40, 42 and 44 of FIG. 2. If the square wave of voltage 78 changes the dimension L by $4.6239 \times 10^{-6}$ cm or by $\lambda/4$, the transmission characteristic of the filter 18 becomes as indicated by the bands 46, 48 and 50. For best results the transmission bands of the filter 18 should have the same shape as the oxygen absorption peaks $N'' = 7$, $N' = 9$ and $N'' = 11$ of the curve $O_2$, and this is largely determined by the reflectivity R of the mirror surfaces 66 and 68. A good match can be attained if $R = 0.9$.

If the lamp 10 contains AsI, the operation illustrated in FIG. 3 can be attained by making $L = 0.00993$ cm and $R = 0.9$ so as to produce a transmission characteristic as indicated by the bands 52 and 54. If the square wave of voltage 78 changes the dimension L by $4.726075 \times 10^{-6}$ cm, or $\lambda/4$, the transmission characteristic of the filter 18 becomes as indicated by the bands 58 and 60.

The spectral transmission of the etalon filter 18 can also be varied so as to shift the bands of wavelengths of light it passes by changing the refractive index of the matter in the gap with temperature, by substitution of different matters in the gap, or by substituting magnetostrictive material for the ring-shaped piezoelectric wafer 70.

The light pipe 24 and the components included within the case 46 form a preferred means for alternately directing two wavelengths of ultraviolet light that are differently absorbed by oxygen to the transparent tube 26 through which the patient breathes, but other means for performing this function may be used. For example, two lamps, one emitting light that is strongly absorbed by oxygen and one emitting light that is weakly absorbed by oxygen could be mounted on a disc that revolves so as to alternately bring them opposite the input aperture 12. In another arrangement, light from the two lamps could be optically superimposed by a rotating mirror at the input aperture 12. Other means such as a diffraction grating could be substituted for the etalon filter 18 for controllably passing either of two bands of ultraviolet light.

Different sources of ultraviolet light could be used such as a deuterium lamp, but whatever the source, the filter 16 is used to reject the wavelengths of light it emits that are not used in making the measurement of oxygen as they could pass through the sample chamber 26 and produce hazardous levels of ozone. The filter 16 could be located at any point in the optical path between the source and the tube 26 through which the patient breathes.

Regardless of the velocity of the gases in the tube 26, the instrument herein described has sufficient accuracy and speed of response to permit the measurements of the concentration of oxygen.

The location of the bands of wavelengths passed by the etalon filter 18 can also be controlled by varying the angle between its normal and the axis of the optical system. This can be achieved with the use of a piezoeletric set-up as shown in FIG. 4 or an electromagnet set-up as shown in FIG. 5.

In FIG. 4 the filter 18 is comprised of transparent plates 80 and 82 separated by a spacer 84 so that the distance L between the interior opposed mirrored surfaces 88 and 90 is 0.0171 cm if the lamp 10 contains HgI and 0.00993 cm if it contains AsI. The etalon filter 18 thus formed is attached by diametrically opposed wafers 92 and 94 to a rigid support 96 that is perpendicular to the optical axis 98, and fixed to the inside of the casing 46. Metallic electrodes 100 and 102 are deposited on opposite sides of the piezoelectric wafer 92, and metallic electrodes 104 and 106 are deposited on opposite sides of the wafer 94. The electrodes 102 and 106 are connected to ground, and either of the electrodes 100 or 104, in this case 100, may be connected to receive square wave 108 from a square wave generator 112. In this way the thickness of the piezoelectric wafers 92 changes so as to tilt the filter 18 with respect to the optical axis 98.

In FIG. 5 the filter 18 is comprised of plates 114 and 116 separated by a spacer 118 so that the interior opposed mirror surfaces 120 and 122 are separated by the distance L. The bottom of the filter 18 is mounted on a spring support 124 so as to be perpendicular to the optical axis 126. A mass 128 of magnetic material is attached to the top of the filter 18, and a stationary electromagnet 130 is driven by square waves 132 from generator 134 so as to cause the angle of the filter 18 to change abruptly between two angular positions with respect to the opticalaxis 126.

FIG. 6 shows another general arrangement of the components of a system incorporating the invention. Those components corresponding in function to components of FIG. 1 are indicated by the same numerals primed. The difference from FIG. 1 lies in the fact that the sample chamber 26' through which the patient breathes is mounted within the casing 46 and preferably between the etalon filter 18' and the focussing lens 20'. No light pipe is needed, and the diode 28' is mounted in the position of the output aperture 22 of FIG. 1.

What is claimed is:

1. An instrument for measuring the concentration of oxygen in a sample containing water vapor and other interfering gases comprising, means providing ultraviolet light of at least two different wavelengths, one of said wavelengths being in a band that is strongly absorbed by oxygen, the other of said wavelengths being in a band that is less strongly absorbed by oxygen, both of said wavelengths being absorbed by water vapor and other interfering gases in nearly equal degree, a sample chamber through which the sample to be examined can be passed, means for alternately directing light of said first and second wavelengths from said means through said chamber, means for developing electrical signals proportional to the amount of light impinging on it, said means being mounted so as to intercept a portion of the light that passes through said chamber, and a narrow band interference filter passing said two different wavelengths of ultraviolet light and rejecting other wavelengths of ultraviolet light that are less than and greater than the two different wavelengths, said filter being in the optical path between said source and said sample chamber.

2. An instrument as set forth in claim 1 wherein said means providing ultraviolet light is a single lamp in which the emission is broadened so as to include said first and second wavelengths.

3. An instrument as set forth in claim 1 wherein said means for alternately directing the light includes an etalon filter having separated plates with opposed interior mirrored surfaces, said etalon filter having a transmission characteristic so as to pass light of the first wavelength when in a first condition and a transmission characteristic so as to pass light of a second wavelength when in a second condition.

4. Apparatus as set forth in claim 3 wherein control means are provided for causing said etalon filter to alternate between said first and second conditions, 5. An instrument as set forth in claim 4 wherein said control means includes means for changing the separation between said plates.

6. An instrument as set forth in claim 4 wherein said control means includes means for tilting said plates.

7. An instrument for measuring the concentration of oxygen flowing in a transparent tube through which a patient breathes comprising, means for alternately directing to said tube two wavelengths of ultraviolet light that are differently absorbed by oxygen, a photoelectric device mounted so as to receive the light after it has passed through said tube and develop electrical signals proportional to the amount of light so received, and means for deriving an output proportional to the alternating component of said electrical signals and an indicator of the concentration of oxygen within the tube.

8. An instrument as set forth in claim 7 wherein said means for alternately directing the two wavelengths of ultraviolet light includes a discharge lamp for emmitting a broad band of ultraviolet light including said two wavelengths, and an etalon filter that can be controlled so as to pass either of the two wavelengths of light.

9. In an instrument for measuring oxygen in a patient's breath, a discharge lamp containing an element that emits ultraviolet light at a plurality of spectral wavelengths, said discharge lamp having means for broadening its emission to include bands of wavelength on either side of each said spectral emission, at least one of said bands including the wavelengths of an absorption peak of oxygen, means defining an input aperture located so as to receive light from said lamp, a lens for collimating light passing through said input aperture, means defining an output aperture,
a lens for focussing collimated light from said collimating lens onto said output aperture,
an etalon filter mounted between said collimating and focussing lenses so as to be traversed by the collimated light,
means for adjusting said etalon filter between a condition where it passes light having a first wavelength coinciding with a wavelength in an absorption peak of oxygen and condition where it passes light of a second wavelength between the wavelengths of absorption peaks of oxygen, and
a narrow band interference filter passing said first and second wavelengths of ultraviolet light and rejecting light having wavelengths outside said first and second wavelengths of light, said filter being located in the optical path between said discharge lamp and said means defining an output aperture.

10. Apparatus for measuring the concentration of oxygen in a patient's breath comprising,
a lamp providing ultraviolet light in a plurality of emission lines, said lamp being such as to broaden the emission about its normal emission lines,
an input aperture mounted in the path of some of the light from said source,
a collimating lens adapted to project light from said input aperture in substantially parallel paths,
a detector,
a focussing lens for focussing collimated light received from said collimating lens on said detector,
a filter mounted in the path of said collimated light for attenuating light associated with all but one of said emission lines,
filtering means mounted in the path of said collimated light that can be controlled so as to alternately pass the ultraviolet light within one broadened emission line that is strongly absorbed by oxygen and ultraviolet light within said broadened emission band that is weakly absorbed by oxygen, and
a sample chamber through which a patient can breathe mounted between said filtering means and said detector.

11. In an instrument for measuring oxygen in patient's breath,
a discharge lamp containing an element that emits ultraviolet light at a plurality of spectral wavelengths,
said discharge lamp having means for broadening its emission to include bands of wavelengths on either side of each said spectral emissions, at least one of said bands including the wavelengths of an absorption peak of oxygen,
means defining an input aperture located so as to receive light from said lamp,
a lens for collimating light received from said input aperture,
means defining an output aperture,
a lens for focussing collimated light from said collimating lens onto said output aperture,
filtering means mounted between said collimating and focussing lenses so as to be traversed by the collimated light,
means for adjusting said filtering means between a condition where it passes light having a first wavelength coinciding with a wavelength in an absorption peak of oxygen and a condition where it passes light of a second wavelength between the wavelengths of absorption peaks of oxygen, and
a narrow band interference filter passing said first and second wavelengths of ultraviolet light and rejecting light having wavelengths outside said first and second wavelengths of light, said filter being located in the optical path between said discharge lamp and said means defining an output aperture.

* * * * *